US005728550A

United States Patent [19]
Fowler et al.

[11] Patent Number: 5,728,550
[45] Date of Patent: Mar. 17, 1998

[54] PEROXIDASE PRODUCTION

[75] Inventors: Michael William Fowler, Nr. Matlock; Gagik Stephan-Sarkissian, Sheffield; Debbie Grey, Chesterfield, all of Great Britain

[73] Assignee: Phytera, Inc., Worcester, Mass.

[21] Appl. No.: 294,880

[22] Filed: Aug. 23, 1994

Related U.S. Application Data

[63] Continuation of Ser. No. 761,833, Nov. 13, 1991, abandoned.

[30] Foreign Application Priority Data

Jan. 15, 1990 [GB] United Kingdom ............... 9000827

[51] Int. Cl.$^6$ ............... C12P 21/04; C12N 9/00; C12N 9/08; C12N 1/00
[52] U.S. Cl. ............... 435/70.1; 424/93.7; 435/28; 435/183; 435/192; 435/243; 435/260; 435/410; 435/420; 435/431; 435/109; 435/118
[58] Field of Search ............... 435/28, 70.1, 183, 435/192, 240.45, 240.46, 240.48, 240.54, 410, 420, 431, 243, 260, 109, 118; 424/93.7

[56] References Cited

U.S. PATENT DOCUMENTS

| | | | |
|---|---|---|---|
| 3,947,324 | 3/1976 | Lakshminarayanan | 195/66 R |
| 4,306,022 | 12/1981 | Kinsella et al. | 435/134 |
| 4,698,306 | 10/1987 | Noda et al. | 435/192 |
| 5,019,504 | 5/1991 | Christen et al. | 435/123 |
| 5,057,424 | 10/1991 | Knuth et al. | 435/240.48 |
| 5,068,184 | 11/1991 | Knuth et al. | 435/41 |
| 5,133,979 | 7/1992 | Clarke et al. | 426/49 |
| 5,296,245 | 3/1994 | Clarke et al. | 426/49 |
| 5,342,765 | 8/1994 | Irvine et al. | 435/71.1 |

FOREIGN PATENT DOCUMENTS

| | | |
|---|---|---|
| 2630429 | 10/1989 | France. |
| 59-028473 | 2/1984 | Japan. |
| 62-138188 | 6/1987 | Japan. |
| 63233782 | 9/1988 | Japan. |
| 1222776 | 9/1989 | Japan. |
| 1222777 | 9/1989 | Japan. |
| 1222778 | 9/1989 | Japan. |
| 2162537 | 2/1986 | United Kingdom. |

OTHER PUBLICATIONS

Forage, "Recovery of Yeast from Confectionery Effluent", pp. 8–9, and p. 80; Jan. 1979.
Moreno et al. "Extracel accumulation ...", 1990, 147–150.
Buckholz, R.G., et al., "Yeast Systems for the Commercial Production of Heterologous Proteins", Bio/Technology, 9:1067–1072 (1991).
Fellinger, A.J., et al., "Expression of the α-Galactosidase from Cyamopsis tetragonoloba (Guar) by Hansenula polymorpha", Yeast, 7:463–473 (1991).
Fowler, M.W., "The Role of Plant Cell Biotechnology in the Production of Plant Derives Therapeutic Agents", Abstract, 2–3 (1992).

Fowler, M.W., "Plant Cell Culture as a Source of Novel medicinal Agents", New Drugs From Natural Sources, 131–140 (post–1991).
Heinstein, P.F., "Plant Cell Suspension Cultures as a Source of Drugs", Pharmacy International 38–41 (1986).
Kutney, J.P., et al., "Studies With Plant Cell Cultures of Podophyllum Peltatum L. I. Production fo Podophyllotoxin, Deoxypodophyllotoxin Podophyllotoxone and 4'-Demethylpodophylltoxin", Heterocycles, 32(12): 2305–2309 (1991).
Linskens, H.F., et al., "Modern Methods in Plant Analysis", Plant Cell Reports 9:173–177 (1990).
Mannonen, et al., "Effects of Long–term Preservation on Growth and productivity of Panax ginseng and Catharanthus roseus Cell Cultures", Plant Cell Reports, 9:173–177 (1990).
Misawa, M., et al., "Production of Antineoplastic Agents by Plant Tissue Cultures", Journal of Medicinal Plant Research, 49:115–119 (1983).
Owen, M.L., et al., "The Expression of Antibodies in Plants", Chemistry & Industry, 406–408 (1992).
Rhodes, M.J.C., et al., "The Use of Plant Cell Cultures in Studies of Metabolism", The Biochemistry of Plants, 13:65–124 (1987).
Roesler, J., et al., "Application of Purified Polysaccharides From Cell Cultures of the Plant Echinacea Purpurea to Test Subjects Mediates Activation of the Phagocyte System", J. Immunopharmac., 13(7):931–941 (1991).
Stafford, A., "New Phramaceuticals From Plant Cell Culture", Agro–Food–Industry Hi–Tech, 9–13 (1992).
Takeda, S., et al., "Nucleotide Sequence of a cDNA for Osmotin–Like Protein from Cultured Tobacco Cells", Plant Physiol. 97:844–846 (1991).
Buckholz et al., Bio/Technology, 38:31–39 (1987).
Czaninski et al., J. Microscopie, 9:1089–1102 (1970).

(List continued on next page.)

Primary Examiner—Michael G. Wityshyn
Assistant Examiner—Deborah Ware
Attorney, Agent, or Firm—Clark & Elbing LLP

[57] ABSTRACT

A process for the production of an extracellular peroxidase using confectionery waste is disclosed. The first step of the process requires culturing a piece of plant tissue containing extracellular peroxidase-producing cells from a plant of the genus Acer, more specifically Acer pseudoplantanus. The culture medium is a solid culture medium and the culturing step is carried out until a callus forms on the solid culture medium. Further, the plant cells produced in the callus are dispersed into a liquid culture medium to form a suspension of plant cell culture. The suspension culture medium contains confectionery waste products which provide 1 to 15% by weight of sugars (i.e. fructose, glucose and sucrose). The culturing of the plant cells in suspension in the liquid culture medium with the concomitant accumulation of the extracellular peroxidase in the liquid culture medium and separating the enzyme therefrom. Also disclosed is a nutrient medium for the plant cell suspension which contains confectionery waste products which provide 1 to 15% by weight of sugars and a concentration of phytohormones is also contained within the nutrient medium for the plant cell suspension.

10 Claims, 3 Drawing Sheets

OTHER PUBLICATIONS

Drotar et al., *Plant Science*, 42:35–40 (1985).
Fellinger et al., *Yeast*, 7:463–473 (1991).
Fowler, *Abstract*, 2–3 (1992).
Fowler, *New Drugs from Natural Sources*, 131–140 (post–1991).
Heinstein, *Pharmacy International*, 38–41 (1986).
Kutney et al., *Heterocycles*, 32(12):2305–2309 (1991).
Lamport, *Exp. Cell. Res.*, 33:195–206 (1964).
Linskens et al., *Plant Cell Reports*, 9:173–177 (1990).
Mannonen et al., *Plant Cell Reports*, 9:173–177 (1990).
Misawa et al., *J. Med. Plant Res.*, 49:115–119 (1983).
Moreno et al., *Plant Cell, Tissue and Organ Culture*, 18:321–327 (1989).
Owen et al., *Chemistry & Industry*, 406–408 (1992).
Rhodes et al., *The Biochemistry of Plants*, 13:65–124 (1987).
Roesler et al., *J. Immunopharmac.*, 13(7):931–941 (1991).
Simola et al., *Physiologia Plantarium*, 23:1212–1222 (1970).
Stafford, *Agro–Food–Industry Hi–Tech*, 9–13 (1992).
Stephan–Sarkissian et al., *4th European Congress on Biotechnology*, 2:342–344 (1987).
Takeda, *Plant Physiol.*, 97:844–846 (1991).
Taya et al., *J. Fermentation and Bioengineering*, 67(1):31–34 (1989).
Yamada et al., *J. Chem. Tech. Biotechnol.*, 38:31–39 (1987).

Peroxidase Activity in Calluses and Cell Suspension Cultures of Radish Raphanus Sativus var. Cherry Bell Moreno et al., (Plant Cell, Tissue and Organ Culture, 1989, 18: 321–327).

Production of Peroxidase with Horseradish Hairy Root Cells in a Two Step Culture System, Taya et al., (Journal of Fermentation and Bioengineering, 1989, vol. 67, No. 1, pp. 31–34).

Some Characteristics of Peroxidase in Plant Cell Cultures, Stepan–Sarkissian et al. (4th European Congress on Biotechnology, 1987, vol. 2, 342–344).

Changes in the Activity of Certain Enzymes of Acer Pseudoplatanus L. Cells at Four Stages of Growth in Suspension Culture Simola et al., (Physiologia Plantarum, 1970, vol. 23, 1212–1222).

Evidence for Glutathione Peroxidase Activities in Cultured Plant Cells Drotar et al., (Plant Science, 1985, 42, 35–40).

Production of Horse Radish Peroxidase by Plant Cell Culture Yamada et al., (J. Chem., Tech. Biotechnol. 1987, 38, 31–39).

Cell Suspension Cultures of Higher Plants: Isolation and Growth Energetics Lamport, (Experimental Cell Research 1964, 33, 195–206).

PEROXIDASE PRODUCTION

This is a continuation of application Ser. No. 07/761,833 filed on Nov. 13, 1991, now abandoned.

This invention relates to a process for the production of peroxidase enzymes from plant cell cultures.

Peroxidase enzymes catalyse a host of reactions in which hydrogen peroxide is a specific oxidising agent and a wide range of substrates act as electron donors. It is widely used at the moment in diagnostic kits, and among other things it has potential use in other industries such as paper recycling, chemical, waste water treatment, and in detergents and bleaching agents.

Peroxidize enzymes are widely distributed in nature and are produced by a wide variety of plant species. At the present time, however, the chief commercial source is horseradish. In the commercial production of horseradish peroxidase (HRP) the horseradish roots are harvested and the sprouted roots are minced mechanically in water to form a starting material. From this, peroxidase is purified by a series of ammonium sulphate and ethanol precipitations. To obtain high purity enzyme, conventional chromatographic techniques are employed. Unfortunately, this process leads to large quantities of waste tissue and problems arise with dispersing of waste. Not only this but there is a significant irreversible loss of enzyme activity resulting from the precipitations with ethanol and ammonium sulphate which are used to extract the enzyme from the tissue. The present invention not only overcomes many of these problems associated with the conventional method for producing peroxidase, it also produces a new peroxidase with improved properties in relatively high yields.

Various other sources have been suggested in the literature for the commercial production of peroxidase. For example, radish plant cell cultures have been suggested as a source of extracellular peroxidase (Plant Cell, Tissue and Organ Culture, 1989, 18:321–327) but the yields and specific activity of the product enzyme are low.

A plant cell culture technique for the production HRPO is disclosed in J. Fermentation Technology, 1989, 67:31–34 based on cultures established from genetically modified horseradish cells, modified to increase the stability of the enzyme.

It has also been suggested that calli cultured from various plant species can be used as a source for the production of peroxidase, but callus culture is inherently incapable of large scale commercial production. Such suggestions are contained in unexamined published Japanese patent applications:

JP-A-1222778 (source species: *Glycyrrhiza glabra* L.var. *Ipomoea batatas* Lam. var deulis Makino, *Stevia rebaudiana* Bertoni, and *Bupleurum falcatum* L.)

JP-A-1222777 (source species: *Zoysia japonica*, and *Zoysia macrostachchya*)

JP-A-1222776 (source species: *Trifolium repens* L., *Carica papaya* L., *Phellodendron amurense* Rupr., *Oenothera lamarchiana* Ser., *Scopolia japonica* Maxim, *Lithospermum erythrorhizon* Sieb et Zucc., *Glycine max* Merrill, and *Gynastema pentaphyllum* Makino.)

JP-A-63233782 (source species: general) JP-A-62138188 (Source species: *Ipomoea aquatica* Forsk.)

Amongst other plants known to produce peroxidase are plants of the genus Acer (sycamore), although, so far as the present applicants are aware, nobody has yet proposed to produce peroxidase commercially from Acer, and certainly not by means of a cell suspension culture. Thus, J. de Microscopie, 1970, 9:1089–1102 reports on the microscopic examination of sycamore leaf tissue and cultured cell sections of sycamore tissue which have been stained using a chromogenic peroxidase substrate to show up the microscopic intra-cellular structures.

In a paper presented to and published in the proceedings of the Fourth European Congress of Biotechnology, 1987, 2:342–344, the present inventors reported the results of a comparative study on the effect of peroxidase in plant cell cultures from four different species including inter alia Acer, with specific reference to the production of intra-cellular peroxidase and its involvement in the degradation of secondary products of the cell suspension culture, but did not identify suspension cultures of Acer as a potential commercial source of a high activity, high yield extra-cellular peroxidase.

In Physiologia Plantarum, 1970, 23:1212–1222 the authors report a study of intra-cellular peroxidase activity in sycamore cells conducted with a view to establishing various metabolic pathways in the plant metabolism, but with no suggestion as to any commercial utility or even any extra-cellular peroxidase activity.

Finally the production of an intra-cellular glutathione peroxidase in sycamore cells has been reported in Plant Science, 1985, 42: 35–40.

In contrast to the foregoing, it has now been found that a highly active, highly stable peroxidase enzyme is produced extra-cellularly in high yield by suspension plant cell cultures of plant cells from plants of the genus Acer, and especially plant cell cultures of *Acer pseudoplatanus*, and especially root cell cultures. The fact that the peroxidase is produced extra-cellularly in high yield (with approximately 80% of the total peroxidase being produced extra-cellularly) is highly surprising, and greatly simplifies product recovery. Indeed for many commercial purposes, it is sufficient merely to separate the supernatant liquor containing the extra-cellular peroxidase from the culture, either batchwise or continuously, to provide a crude peroxidase containing liquor which can be used as such, or which can be further concentrated, if needed, e.g. by evaporation, freeze drying or ultrafiltration. However, if a substantially pure peroxidase is required this can be recovered from the culture liquor by simple separation means, such as chromatography. Either way the risk of deactivation of the enzyme during the recovery and purification procedures is substantially reduced. Also, since such a high proportion of the enzyme is produced extra-cellularly, waste disposal problems are simplified since the volume of cellular tissue remaining at the end of the culture and recovery of the peroxidase is relatively low. If desired, that cellular tissue can be further processed, after completion of the culture and separation of the cultured cells from the supernatant liquor, to recover intra-cellular peroxidase as an additional product, thus contributing considerably to the over all economies of the process. That intra-cellular peroxidase may be recovered, for example, by the established procedures of disrupting the cells to release the intra-cellular peroxidase followed by extraction and precipitation with ethanol and ammonium sulphate in the conventional way.

In accordance with a first aspect, therefore, of the present invention, there is provided a process for the production of peroxidase enzyme which comprises establishing a plant cell culture of extra-cellular peroxidase producing cells from a plant of the genus Acer in suspension in a culture medium capable of supporting the growth of the extra-cellular peroxidase producing cells, continuing the culture of said cells in suspension in the culture medium with the concomitant accumulation of extra-cellular peroxidase in the culture medium, and recovering the accumulated peroxidase from the culture medium.

The resulting extra-cellular peroxidase has advantageous properties over the conventional horseradish peroxidase. Included among these properties are a high initial level of activity and an improved thermal stability at high temperatures. This is very useful in some industries where a reaction may be more effective at a higher working temperature but is unable to operate there due to the very sensitive nature of enzymes which denature under adverse thermal conditions. Additionally, the peroxidase according to this invention has a high storage stability.

Thus in a second aspect in this invention there is provided in substantially pure form peroxidase enzyme having the following characteristics:

Source: *Acer pseudoplatanus*

Location: Extra-cellular

Mol.wt.(Gel. Filtration): Approx. 37000 pH range: 4–9

Optimum pH: 5.5

Optimum assay temperature: 45° C.

Stability: Retains at least 50% of optimum activity at 65° to 75° C.

Reactivity: Substantially $H_2O_2$ specific, but reactive in the presence of: guaiacol, pyrogallol, aminophenol or O-dianisidine as the reductant.

Elution profile: Six distinct activity peaks—see FIG. 4.

The process of the present invention begins with the initiation and maintenance of a suspension culture of the extra-cellular peroxidase producing Acer plant cells, preferably *Acer pseudoplatanus*. This is best achieved by germinating the Acer seeds, preferably seeds of *Acer pseudoplatanus* on a suitable growth medium, e.g. agar, excising root tissue from the germinated seeds, transferring the excised root tissue on to fresh growth medium and continuing the growth of the root tissue in said fresh medium to produce root tissue calli, which can then be comminuted and transferred into a liquid growth medium to establish a suspension culture of the root tissue. This initial culture can then be subcultured to provide for the large scale production and accumulation of extra-cellular peroxidase in the culture medium.

As the culture media for the callus and suspension cultures there may be used any suitable culture medium for plant cell cultures, e.g. Gamborgs B5 medium or Murashige and Skoog (MS) medium containing a suitable carbon source, e.g. one or more of glucose, sucrose and fructose in an amount of from 1–15% by weight, preferably from about 2–5% and most preferably about 3%, and the necessary phytohormones, e.g. dichlorophenoxyacetic acid and kinetin. For the callus culture Gamborgs B5 medium is preferably used. For the suspension (production) culture the preferred medium is the MS medium.

A characteristic feature of the plant cell cultures used in accordance with the present invention, particularly the root cell cultures of *Acer pseudoplatanus* is that it has been found possible to use carbohydrate waste materials containing glucose and/or sucrose, such as are produced in large amounts in the confectionery industry, as the carbon source in the culture medium, rather than the customarily used refined glucose and/or sucrose. Glucose and/or sucrose containing wastes produced in the confectionery industry, e.g. floor sweepings, mis-shapen moulded confectioneries and discontinued lines, present a substantial disposal problem in the confectionery industry since it is usually not economic to reprocess the waste, and simply dumping the waste presents environmental problems. In accordance with the present invention, it has been found that such wastes provide an inexpensive source of glucose and/or sucrose for the plant cell cultures and which can be supplied simply by extracting the waste confectionery with water and feeding the crude extract, without further purification or refinement, to the culture medium, the plant cell culture being remarkably tolerant to the other water soluble ingredients, dyes etc. in the waste confectionery. The necessary phytohormones used in the medium are 2,4-dichlorophenoxyacetic acid at around 1 mg. $L^{-1}$ and 6-furfurylaminopurine (kinetin) at around 0.1 mg. $L^{-1}$.

Aerobic culture conditions are used preferably at a pH from 5.6 to 5.8 and at a temperature of about 25° C., with optimum peroxidase activity occurring in the culture medium after about 8 days of continuous culture.

A preferred method according to this invention will now be described in detail with reference to the production of extra-cellular peroxidase from *Acer pseudoplatanus* cell cultures, and with reference to the accompanying drawings, in which.

Initiation and maintenance of the cell culture

Sycamore cell cultures are initiated from root tissue of *Acer pseudoplatanus* by first germinating seeds of *A. pseudoplatanus* on agar medium. The seeds are first sterilised by immersion in 15% hypochlorite solution with shaking on a gyrotatory shaker for approximately 40 minutes at 24° C. After this sterilisation, the seeds are washed with copious amounts of sterile distilled water to remove all traces of hypochlorite. The seeds are then placed on agar and incubated at 25° C. After germination, small segments of root are excised aseptically and transferred onto fresh agar medium. Periodically the tissue is examined for callus formation. Callus cultures are then initiated and established by routine subculture, following which portions of the callus culture tissue are transferred into a liquid culture medium to establish the cell suspension culture. During the establishment of the suspension culture viability tests are carried out on the cell lines using the fluorescin diacetate method (described below). In this way the suspension cultures can be subcultured by volume on a fortnightly basis, i.e. they can be maintained routinely by the aseptic transfer of 20 mL amounts of 14 day old cultures into 100 mL aliquots of sterilised culture medium in 250 ml Erlenmeyer flasks. The flasks are placed on a gyrotatory shaker at 150 rpm in the light at 25° C.

The cell line is initiated on B5 medium (Gamborg et al., Exp. Cell Res. 50, 148–151, 1968) with 3% sucrose as the carbon source, but is later transferred on to Murashige & Skoog (MS) medium (Murashige et al. Physiol. Plant 15, 473–497, 1962) with 3% glucose as the carbon source. The phytohormones added to the medium are 1 mg.$L^{-1}$ 2,4-dichlorophenoxyacetic acid and 0.1 mg.$L^{-1}$ 6-furfurylaminopurine (kinetin). The pH of the growth medium is adjusted to 5.6–5.8 prior to sterilisation.

Sycamore culture details

For small scale experimental work the cultures are subcultured by weight, i.e. 3 g fresh weight per 100 ml medium.

For intermediate scale experiments (up to 10 L), two litres of 14 day old culture can be used as inoculum in 8 L of fresh medium in a reaction vessel equipped with a stirrer. Suitable intermediate scale culture conditions include pH 5.6 to 5.8 temperature 25° C. and a compressed air feed of about 1 Lmin$^{-1}$.

Large scale cultures can be conducted in similar manner in an LH (Registered TM) 30 L airlift fermentor, for example by inoculation with 14 day old root cell cultures sufficient to give a fresh weight of 20 g. L$^{-1}$ (approximately 2.0 g.L$^{-1}$ dry weight). The vessel is aerated with compressed air at a rate of 6 L.min$^{-1}$ and at a temperature of 25° C.

Figure 1:
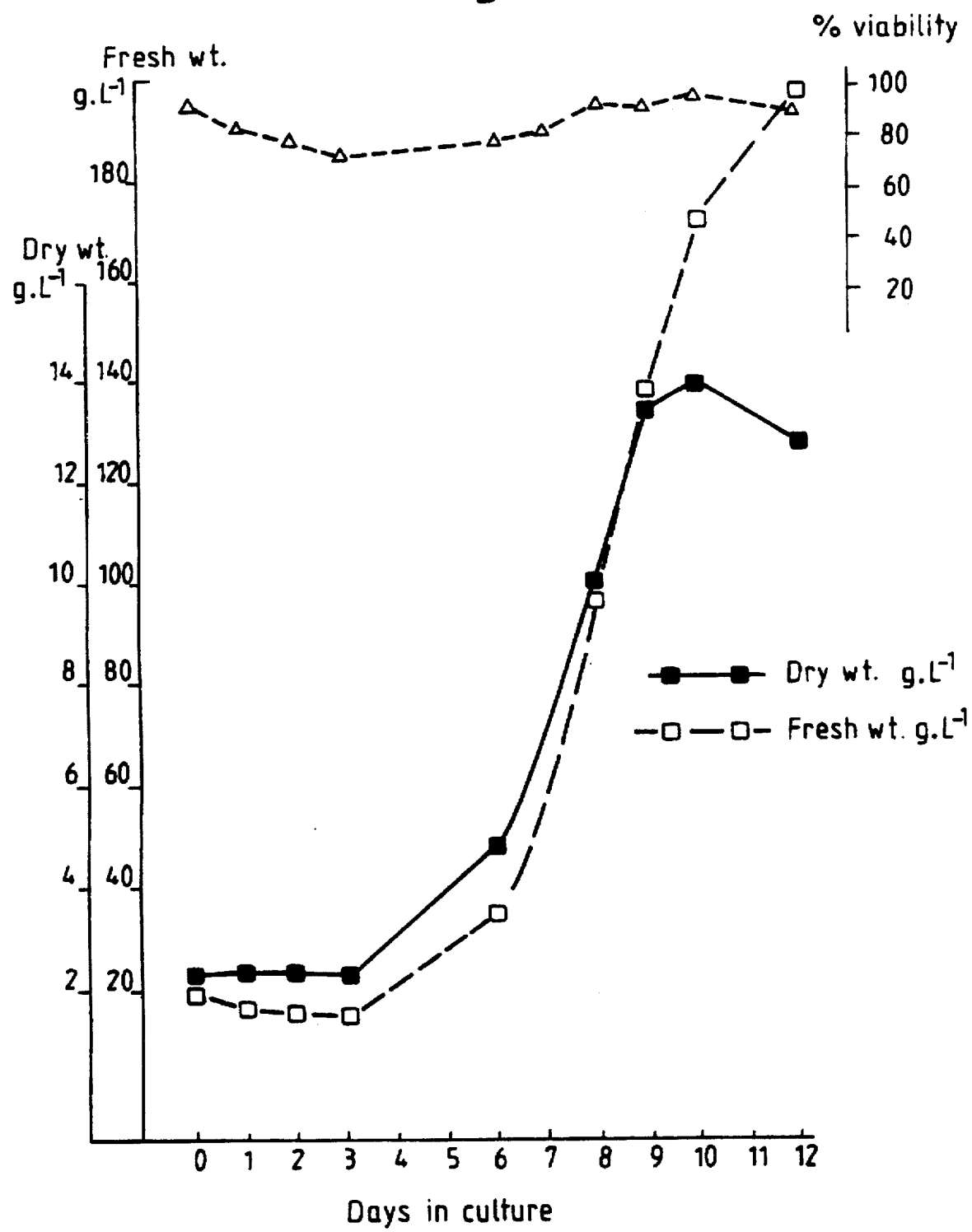
FIG. 1 shows the growth profile of *A. pseudoplatanus* root cell cultures in MS medium supplied with 3% sucrose/glucose in a 30 L airlift fermentor.

FIG. 1 of the accompanying drawings shows a growth profile for a sycamore culture grown in a 30 L airlift fermentor. This shows an optimum cell viability after 9 days in the fermentor, an optimum cell fresh weight after 11 days in the fermentor and an optimum cell dry weight after 10 days in the fermentor.

Experimental methods

By aseptically taking small culture samples from the culture vessel at regular intervals, and monitoring fresh and dry weight measurements, cell viability, culture pH and peroxidase activity, it is possible to determine an optimum culture time and optimum conditions for the efficient production of peroxidase. These experiments are detailed below:

Fresh and dry weight measurements

A Whatman (Registered Trade Mark) No. 1 filter paper disc, 2.5 cm in diameter, is weighed directly after its removal from an oven where it has been drying at 60° C. for at least 24 hours. The disc is then placed on a stainless steel filter bed seated on a rubber stopper in a Buchner flask. The disc is wetted with distilled water and a vacuum applied to the flask for approximately 10 seconds to remove excess water. The wet filter disc is then weighed immediately. The disc was replaced on the filter bed and the filter top is positioned directly over the disc. A 3 mL portion of culture is filtered through the system and a vacuum applied to remove any excess of medium. The disc with the cells thereon is weighed immediately and placed in an oven at 60° C. for at least 24 hours before being reweighed. Calculations of the fresh and dry weights of the cultures are made using the following equations:

$$\text{Wet weight (g/L)} = \left\{ \frac{\text{Wt of wet (disc + cells)} - \text{wt of wet disc}}{\text{Sample volume (mL)}} \right\} \times 1000$$

$$\text{Dry weight (g/L)} = \left\{ \frac{\text{Wt of dry (disc + cells)} - \text{wt of dry disc}}{\text{Sample volume (mL)}} \right\} \times 1000$$

Viability tests

One drop of culture together with one drop of fluorescin diacetate solution (1:50 dilution with water of a stock solution made up of 5 mg fluorescin diacetate in 1 ml acetone) is placed on a cavity microscope slide and a cover slip placed over it. After approximately 2 minutes the resulting fluorescence is observed using a fluorescence microscope equipped with an exciter filter. Viable cells exhibit a bright green fluorescence. Culture viability is estimated by counting the number of cells that fluoresce in a given field and expressing this as a percentage of the total number of cells in that field.

Estimation of peroxidase activity

Firstly the samples from the culture are fractionated into cell and medium fractions in order to determine the peroxidase activity in each.

The cells are disrupted on ice using a pre-chilled mortar and pestle with approximately 10% (w/w) pre-chilled, acid-washed sand and ice cold 0.1M McIlvaine's citric acid phosphate buffer* pH 5.5. An Eppendorf system was used to centrifuge the cell homogenate for 2 minutes to remove the sand and debris. The resulting supernatant was transferred to clean tubes and centrifuged for a further 5 minutes. The supernatant was carefully removed from the centrifuge tube and kept on ice before use.

(* McIlvaine's citric acid phosphate buffer: 43.10 ml 0.1M citric acid and 56.90 ml 0.2M disodium phosphate).

Peroxidase assay

Peroxidase catalyses a host of reaction in which hydrogen peroxide is a specific oxidising agent and a wide range of substrates act as electron donors.

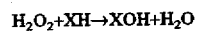
$H_2O_2 + XH \rightarrow XOH + H_2O$

The electron donor used in the assay described in this application is guaiacol (Bergmeyer, 1983).

$H_2O_2 + 4\ \text{guaiacol} \rightarrow H_2O + \text{tetra-guaiacal}$ In this case the assay mixture is prepared as follows:

| | Assay Mixture | |
|---|---|---|
| | For Medium Enzyme | For Cell Enzyme |
| 0.1M McIlvaine's citric acid phosphate buffer, pH 5.5 | 2.80 mL | 2.84 mL |
| 0.15M guaiacol (18.3 g.L$^{-1}$) | 0.10 mL | 0.10 mL |
| 43.7 mM H$_2$O$_2$ | 0.04 mL | 0.04 mL |
| Cell extract | — | 0.02 mL |
| Medium | 0.06 mL | — |

The reaction is started by the addition of hydrogen peroxide. Although the volume of cell extract is altered depending upon the activity of the enzyme, however the total assay volume is maintained at 3.0 ml by a corresponding change in the volume of buffer used. The appearance of tetra-guaiacal, i.e. an increase in absorbence at 436 nm, is monitored during the reaction at 25° C.

Peroxidase activity (units/ml) in the cell extract and the medium is calculated according to the formula:

$$\text{Activity Units/mL} = \frac{\text{A/min} \times 4 \times \text{reaction volume (mL)}}{25.5 \times \text{sample volume (ml)}}$$

One unit of enzyme activity is defined as µmoles of substrate utilised per minute. Where A/min is the change in absorbence per minute at 436 nm, and the constant 25.5 is the molar extinction coefficient (cm$^2$/mole) for tetra-guaiacal.

Figure 2:
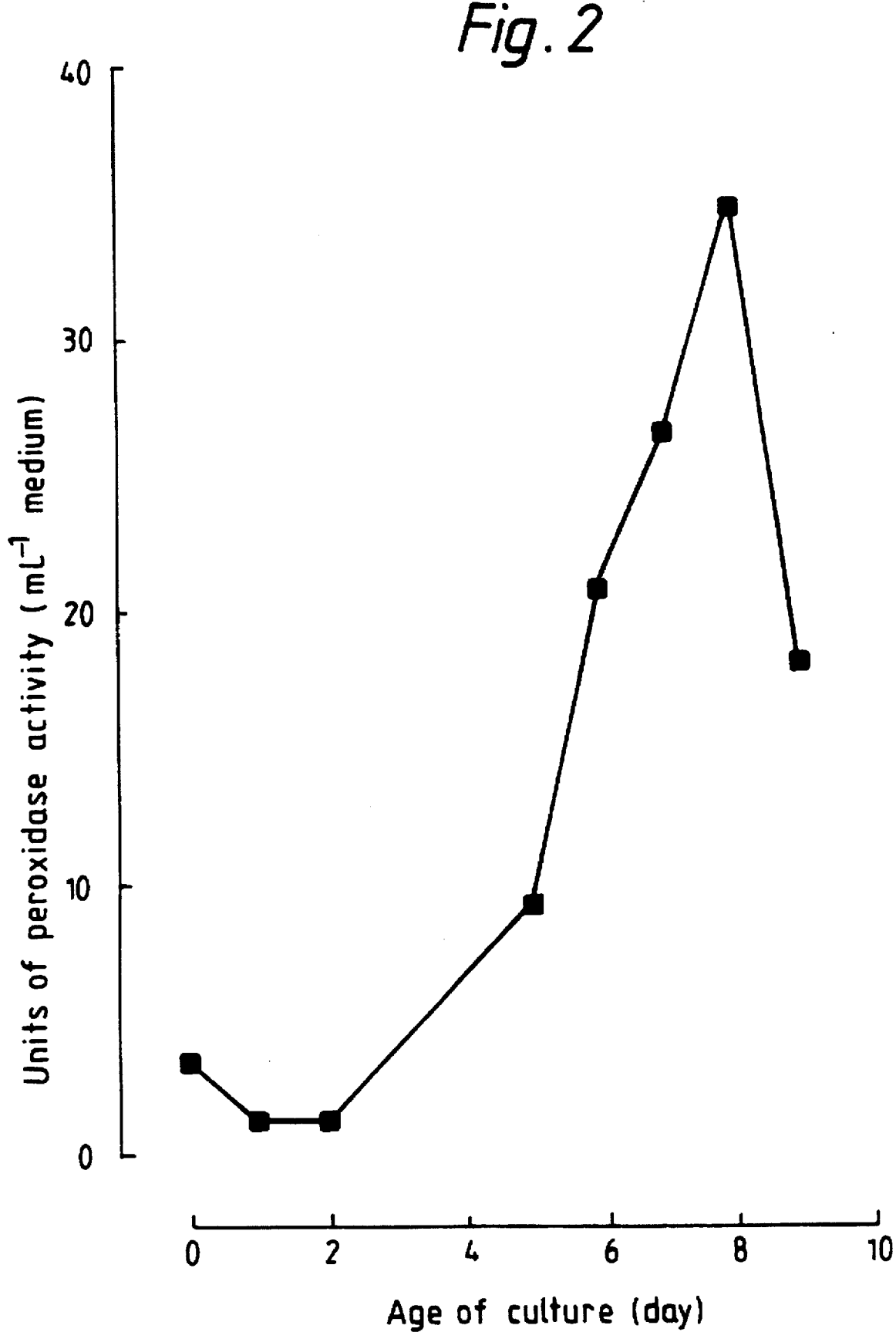
FIG. 2 shows the extra-cellular peroxidase production profile of *A. pseudoplatanus* root cell culture in MS medium supplied with 3% sucrose/glucose in a 250 mL Erlenmeyer flask.

FIG. 2 of the accompanying drawings represents a graph showing the peroxidase production profile in the medium from a suspension root cell culture of *Acer psuedoplatanus* in 250 mL Erlenmeyer flasks. On day 8 of culture there is a substantial increase in medium peroxidase activity to reach 34,500 units per litre of medium. This level of activity corresponds to approximately 80% of total peroxidase activity in the culture. Thus it would appear that day 8 of the culture is optimum for the extraction of peroxidase.

Extraction of peroxidase from the culture is achieved by conventional downstream processing techniques, and here the advantage of this process lies in the fact that approximately 80% of the peroxidase is present in the culture medium and therefore is relatively easily extracted. After separating the cells from the medium, the latter is concentrated using ultrafiltration by first passing the liquor through a 100,000 molecular weight cut-off filter, followed by a 20,000 molecular weight cut-off filter. For high purity enzyme conventional chromatography techniques can be employed.

The characteristics of the peroxidase product obtained are as follows:

Molecular weight (gel filtration): about 37000;

pH range: 4 to 9;

Optimum pH: 5.5;

Optimum assay: 45° C.

Figure 3:
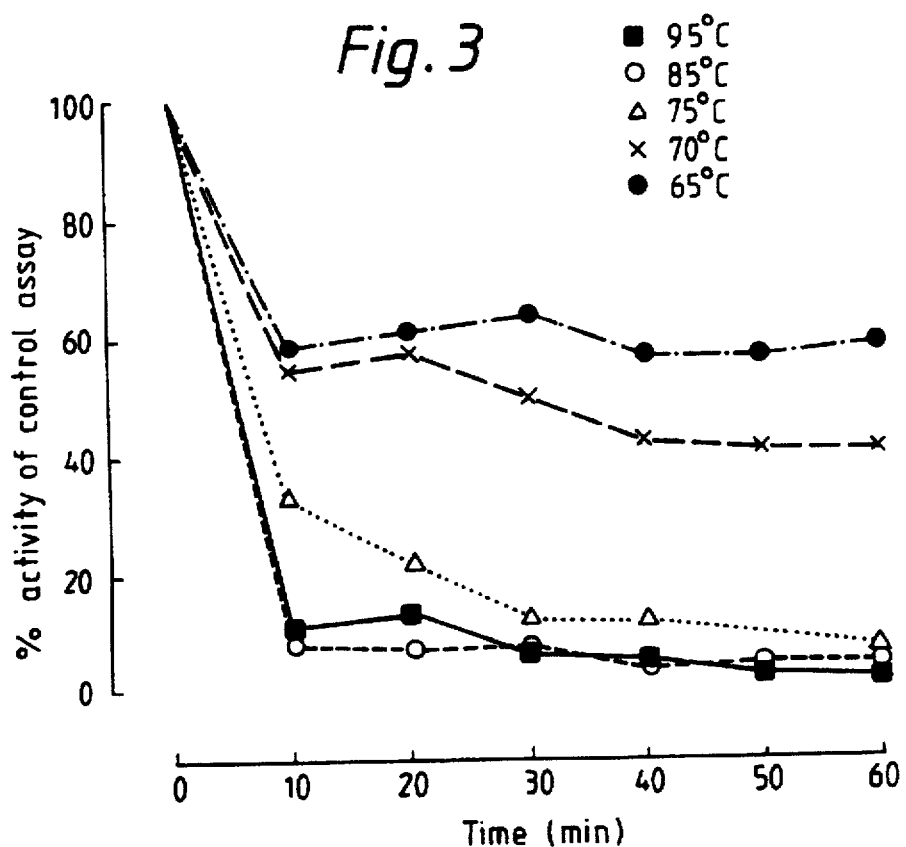
FIG. 3 shows the thermal stability profile of the *A. pseudoplatanus* extra-cellular peroxidase.

Temperature stability: As shown by accompanying FIG. 3, the peroxidase retains approximately 50% of its original activity when heated at 65° to 70° C. for one hour, after an initial decrease in activity over the first 10 minutes. Other tests have shown that some activity is retained even after heating to 95° C.

Storage stability: The peroxidase has been shown to retain its activity for prolonged periods of time, e.g. 12 months or more at temperatures of from +4° C. to −20° C. The enzyme can be stored in crude form, as a suspension in ammonium sulphate or freeze dried.

Figure 4:
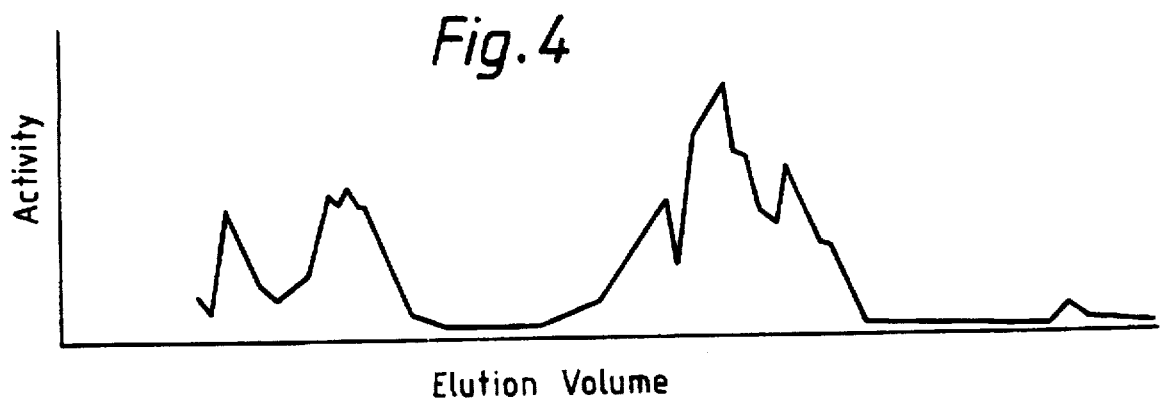
FIG. 4 shows the elution profile.

Elution profile: When eluted from a Whatman CM52 ion-exchange column using a gradient of 0.01 to 1.0M sodium acetate buffer at pH 5.0, a characteristic 6- peak profile is obtained, see FIG. 4.

We claim:

1. A process for the production of an extracellular peroxidase comprising the steps of:

culturing a piece of plant tissue containing extracellular peroxidase-producing cells from a plant of the genus Acer on a solid culture medium until a callus forms;

dispersing plant cells in the callus into a liquid culture medium to form a suspension culture, wherein the suspension culture medium contains confectionery waste products which provide 1–15% by weight of sugars selected from the group consisting of fructose, glucose and sucrose;

continuing the culture of said plant cells in suspension in the liquid culture medium with the concomitant accumulation of the extracellular peroxidase in the liquid culture medium; and separating the accumulated extracellular peroxidase from the liquid culture medium.

2. The process of claim 1, wherein the extracellular peroxidase producing plant cells are cells from the species *Acer pseudoplatanus*.

3. The process of claim 2, wherein the cells are cultured in the suspension culture under aerobic conditions at a temperature of about 25° C., and at a pH in the range of 5.6 to 5.8.

4. The process of claim 1, wherein the extracellular peroxidase producing plant cells are derived from root cells.

5. A process of claim 4, wherein the extracellular peroxidase-producing plant cells are cells from the species *Acer pseudoplatanus*.

6. The process of claim 4, wherein said step of culturing a piece of plant tissue on solid culture medium comprises germinating plant seeds from a plant of the genus Acer on a solid culture medium, transferring sections of root tissue from the germinated seeds to fresh solid culture medium, and allowing the transferred root tissue to form the callus.

7. The process of claim 1, further comprising the steps of separating the liquid culture medium from the cultured plant cell tissue to provide a supernatant liquor containing the accumulated extracellular peroxidase, and recovering intracellular peroxidase from the separated plant cell tissue as a product separate from extracellular peroxidase.

8. The process of claim 7, wherein said step of recovering intracellular peroxidase from the separated plant cell tissue includes disrupting the cells in said separated plant cell tissue, extracting the intracellular peroxidase from the disrupted plant cells with ethanol, and precipitating the extracted intracellular peroxidase with ammonium sulfate.

9. The process of claim 1, wherein extracellular peroxidase is recovered from the culture by separating supernatant peroxidase-containing liquor to produce a crude peroxidase-containing extract.

10. A plant cell suspension culture medium for the genus Acer comprising confectionery waste products which provide 1–15% by weight of sugars selected from the group consisting of fructose, glucose, sucrose and a combination thereof; and an effective mount of a phytohormone.

* * * * *

UNITED STATES PATENT AND TRADEMARK OFFICE
CERTIFICATE OF CORRECTION

PATENT NO.   5,728,550
DATED        March 17, 1998
INVENTORS    Michael William Fowler, Gagik Stephan-Sarkissian, and Debbie Grey It is certified that error appears in the above-identified patent and that said Letters Patent is hereby corrected as shown below:

On the title page,

Under References Cited, Other Publications

Fowler Reference, second line, replace "Derives" with --Derived--.

Stafford Reference, first line, replace "Phramaceuticals" with --Pharmaceuticals--.

Under Abstract

Fifth line, replace "*pseudoplantanus*" with --*pseudoplatanus*--.

Column 1, line 64, replace "Acer" with --*Acer*--.

Column 1, line 66, replace "Acer" with --*Acer*--.

Column 2, line 10, replace "Acer" with --*Acer*--.

Column 2, line 29, replace "Acer" with --*Acer*--.

Column 2, line 64, replace "Acer" with --*Acer*--.

Column 3, line 32, replace "Acer" with --*Acer*--.

Column 3, line 34, first instance, replace "Acer" with --*Acer*--.

UNITED STATES PATENT AND TRADEMARK OFFICE
CERTIFICATE OF CORRECTION

PATENT NO. : 5,728,550
DATED : March 17, 1998
INVENTORS : Michael William Fowler, Gagik Stephan-Sarkissian, and Debbie Grey It is certified that error appears in the above-identified patent and that said Letters Patent is hereby corrected as shown below:

Column 4, line 48, replace "fluorescin" with --fluorescein--.

Column 5, line 53, replace "fluorescin" with --fluorescein--.

Column 5, line 55, replace "fluorescin" with --fluorescein--.

Column 6, line 12, replace "reaction" with --reactions--.

Column 6, line 50, replace "absorbence" with --absorbance--.

Column 7, line 34, replace "Acer" with --*Acer*--.

Column 8, line 16, replace "Acer" with --*Acer*--.

Column 8, line 38, replace "Acer" with --*Acer*--.

Column 8, line 42, replace "mount" with --amount--.

Signed and Sealed this

Sixth Day of October, 1998

Attest:

BRUCE LEHMAN

*Attesting Officer*  *Commissioner of Patents and Trademarks*